United States Patent
Lee

(10) Patent No.: US 11,434,496 B2
(45) Date of Patent: Sep. 6, 2022

(54) RECOMBINANT VECTOR COMPRISING BIP FRAGMENT AND PREPARATION METHOD OF RECOMBINANT PROTEINS USING THEREOF

(71) Applicant: BIOAPPLICATIONS INC., Pohang-si (KR)

(72) Inventor: Yongjik Lee, Pohang-si (KR)

(73) Assignee: BIOAPPLICATIONS INC., Pohang-si (KR)

( * ) Notice: Subject to any disclaimer, the term of this patent is extended or adjusted under 35 U.S.C. 154(b) by 112 days.

(21) Appl. No.: 16/637,116

(22) PCT Filed: Dec. 6, 2018

(86) PCT No.: PCT/KR2018/015400
§ 371 (c)(1),
(2) Date: Feb. 6, 2020

(87) PCT Pub. No.: WO2020/059962
PCT Pub. Date: Mar. 26, 2020

(65) Prior Publication Data
US 2020/0263191 A1    Aug. 20, 2020

(30) Foreign Application Priority Data
Sep. 19, 2018 (KR) .......................... 10-2018-0112444

(51) Int. Cl.
*C12N 15/82* (2006.01)
*C07K 14/005* (2006.01)

(52) U.S. Cl.
CPC ........ *C12N 15/8242* (2013.01); *C07K 14/005* (2013.01); *C12N 15/8221* (2013.01)

(58) Field of Classification Search
None
See application file for complete search history.

(56) References Cited

U.S. PATENT DOCUMENTS

2012/0219580 A1* 8/2012 Hwang .................. A61P 37/04
424/192.1
2015/0121561 A1* 4/2015 Koivu ................ C12N 15/8257
800/260

FOREIGN PATENT DOCUMENTS

| KR | 10-2011-0023485 A | 3/2011 |
| KR | 10-1262300 B1 | 5/2013 |
| KR | 20160077239 A * | 7/2016 |
| KR | 10-2017-0043793 A | 4/2017 |
| KR | 10-1732624 B1 | 5/2017 |
| KR | 10-1848082 B1 | 4/2018 |
| KR | 10-2018-0084680 A | 7/2018 |
| WO | 2011/025242 A2 | 3/2011 |

OTHER PUBLICATIONS

UniProt Accession Q9LKR3, entry version 120 dated Oct. 1, 2014. (Year: 2014).*
NCBI, NCBI Reference Sequence No. NP_198206.1, 'heat shock protein 70 (Hsp 70) family protein [*Arabidopsis thaliana*]', Mar. 20, 2017.

* cited by examiner

*Primary Examiner* — Charles Logsdon
(74) *Attorney, Agent, or Firm* — Vorys, Sater, Seymour and Pease LLP; Mih Suhn Koh

(57) ABSTRACT

Provided is a recombinant vector including a new BiP gene fragment, and when a target protein is prepared using the recombinant vector of the subject matter, use stability can be enhanced and the production amount of target protein can also be increased by minimizing a foreign peptide sequence remaining in the target protein.

22 Claims, 2 Drawing Sheets
Specification includes a Sequence Listing.

RECOMBINANT VECTOR COMPRISING BIP FRAGMENT AND PREPARATION METHOD OF RECOMBINANT PROTEINS USING THEREOF

CROSS-REFERENCE TO RELATED APPLICATIONS

This application is a 371 of PCT/KR2018/015400, filed Dec. 6, 2018, which claims the benefit of priority from Korean Patent Application No. 10-2018-0112444, filed Sep. 19, 2018, the contents of each of which are incorporated herein by reference in its entirety.

SEQUENCE LISTING

The Sequence Listing submitted in text format (.txt) filed on Feb. 6, 2020, named "SequenceListing.txt", created on Dec. 16, 2019 (7.34 KB), is incorporated herein by reference.

TECHNICAL FIELD

The present invention relates to a recombinant vector comprising a new BiP fragment and a method for preparing a recombinant protein using the vector.

BACKGROUND ART

A biopharmaceutical refers to the use of a material present in vivo as a pharmaceutical, and may be defined in a broader sense as a pharmaceutical produced based on biotechnology such as gene recombination, cell fusion, and cell culture, which is advanced biotechnology. These biopharmaceuticals are classified into protein pharmaceuticals, therapeutic antibodies, vaccines, gene therapeutics, cell therapeutics, and the like. Among them, protein pharmaceuticals, therapeutic antibodies, and the like are generally produced using a host such as yeast, bacteria, animal cells, and insect cells, and recently, there is a trend of the increasing use of these pharmaceuticals. Accordingly, there is a continuous need for developing a method that increases the production amount of recombinant protein, simultaneously easily isolates the recombinant protein, and can enhance the stability of the recombinant protein.

Meanwhile, remarkable developments in molecular biology and genetic engineering technology have been applied to the field of plants, and thus, efforts to produce useful physiologically active materials from plant bodies have been continuously made. The production of useful materials from plants has desirable advantages in that not only the unit cost of production may be remarkably reduced, but also it is possible to eliminate various contamination sources (viruses, oncogenes, enterotoxins, and the like) that may be occur in common methods in the related art (methods for synthesizing, isolating, and purifying a protein from animal cells or microorganisms) from the beginning and to manage the seed stock with seeds even in the commercialization stage, unlike animal cells or microorganisms (Korean Patent No. 10-1848082).

Therefore, when a production system of a recombinant protein, which can also be used for plant bodies, can remarkably increase the production amount of recombinant protein, and can enhance the use stability of the recombinant protein by minimizing a foreign peptide sequence that is added during the preparation of the recombinant protein, is developed, it is expected to be able to produce the recombinant protein required for various fields with high efficiency.

DISCLOSURE

Technical Problem

The present invention has been devised to solve the aforementioned problems in the related art, and an object thereof is to provide a gene construct comprising a new BiP fragment and a polynucleotide encoding a target protein, a recombinant vector including the gene construct, a method for preparing a recombinant protein using the vector, and the like.

However, the technical problems which the present invention intends to solve are not limited to the technical problems which have been mentioned above, and other technical problems which have not been mentioned will be apparently understood by a person with ordinary skill in the art to which the present invention pertains from the following description.

Technical Solution

The present invention provides a gene construct in which a BiP gene fragment represented by SEQ ID No. 6 and a polynucleotide encoding a target protein are sequentially linked so as to be operable. The sequential linkage may be in a form in which the polynucleotide encoding the target protein is linked to an N terminal and/or C terminal of the BiP gene fragment, but is not limited thereto as long as it is in a form in which the polynucleotide encoding the target protein is linked to the BiP gene.

Further, the present invention provides a recombinant vector including a gene construct in which a promoter gene, a BiP gene fragment represented by SEQ ID No. 6, and a polynucleotide encoding a target protein are sequentially linked so as to be operable.

In an embodiment of the present invention, the gene construct minimizes a foreign peptide that is added in the production of the target protein, or increases the expression level of the target protein.

In another embodiment of the present invention, the promoter is a 35S promoter derived from the cauliflower mosaic virus, a 19S RNA promoter derived from the cauliflower mosaic virus, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, a pEMU promoter, an MAS promoter, a histone promoter, a Clp promoter, and the like, but is not limited thereto as long as it is a promoter known to be able to be used for a recombinant vector.

In still another embodiment of the present invention, the target protein may be an antigen, an antibody, a fragment of an antibody, a structural protein, a regulatory protein, a transcription factor, a toxin protein, a hormone, a hormone analog, a cytokine, an enzyme, a fragment of an enzyme, an enzyme inhibitor, a transport protein, a receptor, a fragment of a receptor, a biological defense inducer, a storage protein, a movement protein, an exploitive protein, a reporter protein, and the like, but is not limited as long as it is a protein that may be prepared by a recombinant expression vector of the present invention.

In yet another embodiment of the present invention, the recombinant vector may additionally include a gene encoding a His-Asp-Glu-Leu (HDEL) peptide, a 5' untranslated region (UTR) site gene of M17, a tag gene for high expression of a target protein, a tag gene for easy isolation of a target protein, and the like.

In addition, the present invention provides a transgenic organism transformed with the recombinant vector.

In an embodiment of the present invention, the transgenic organism may be a microorganism such as *Escherichia coli, Bacillus, Salmonella*, and yeast, an animal cell including an insect cell and a human, an animal such as a mouse, a rat, a dog, a monkey, a pig, a horse, and a cow, *Agrobacterium tumefaciens*, a plant, and the like, the plant may be food crops including rice, wheat, barley, corn, soybean, potatoes, wheat, red bean, oats, and sorghum; vegetable crops including *Arabidopsis*, Chinese cabbage, white radish, peppers, strawberries, tomatoes, watermelons, cucumbers, cabbages, oriental melons, pumpkins, spring onions, onions, and carrots; specialty crops including ginseng, tobacco, cotton, sesame, sugarcane, sugar beets, perilla, peanuts, and rape; fruit trees including apple trees, pear trees, jujube trees, peach trees, grape trees, tangerine trees, persimmon trees, plum trees, apricot trees, and banana trees; flowering plants including roses, carnations, chrysanthemum, lilies, and tulips, and the like, but is not limited thereto as long as it may be an organism which may be transformed with the recombinant expression vector of the present invention.

Further, the present invention provides a method for producing a target protein, the method including: (a) culturing the transgenic organism; and (b) isolating and purifying a target protein from the transgenic organism or culture solution. The transgenic organism may be preferably a cell itself, or a culture product including the cell, and the culture solution may be preferably a culture solution from which cells are removed after the cells are cultured, but is not limited thereto as long as it includes a recombinant protein of the present invention.

In an embodiment of the present invention, the isolating of the target protein may use preferably a sodium phosphate solution supplemented with Triton X-100, imidazole, and sodium chloride (NaCl), and the sodium phosphate solution is a 10 to 100 mM sodium phosphate solution (pH 7.1 to 7.5) supplemented with 0.05 to 0.5 wt % of Triton X-100, 10 to 100 mM imidazole, and 100 to 500 mM NaCl, but is not limited thereto as long as it is generally an extraction buffer used for isolating a protein.

In addition, the present invention provides a recombinant protein in which a BiP fragment represented by SEQ ID No. 7, a linker sequence, and a target protein are sequentially linked.

Advantageous Effects

Since the recombinant vector including the new BiP fragment according to the present invention can enhance the use stability of a recombinant protein and simultaneously increase the production amounts of target proteins by linking polynucleotides encoding various target proteins to the BiP fragment to minimize a foreign peptide sequence added when the target proteins are prepared, the recombinant vector is widely applied to target proteins having various activities, and thus, is expected to be able to produce recombinant proteins in various fields with high efficiency.

MODES OF THE INVENTION

Figure 1:
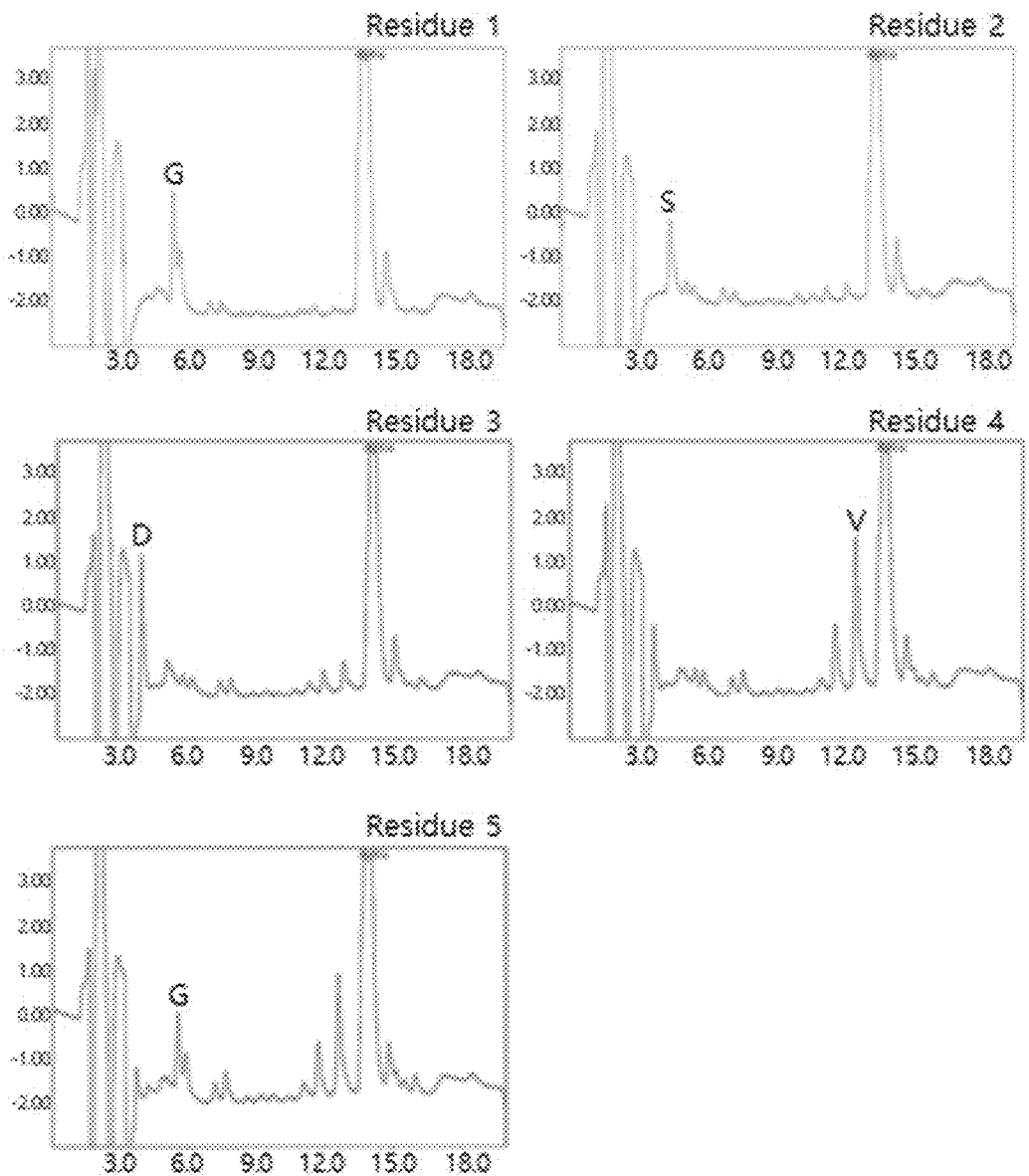
FIG. 1 is a view illustrating results confirming the amino acid sequences of recombinant proteins using a protein sequencing system according to an example of the present invention.

An object of the present invention is to confirm a remaining (fused) residual sequence in a recombinant protein after the recombinant protein is produced among the BiP sequence that was previously used to move the recombinant protein to the endoplasmic reticulum, to confirm that the use stability of the recombinant protein is enhanced and the expression level of the recombinant protein is increased by removing some of the residual sequences to minimize a residual sequence remaining in the recombinant protein, that is, a foreign peptide sequence, and to provide a recombinant vector including the new BiP gene and a method for producing a recombinant protein using the recombinant vector.

In the present specification, the "new chaperone binding protein (BiP) gene fragment" is a portion of the BiP sequence used in order to move an expressed recombinant protein to the endoplasmic reticulum during the preparation of the existing recombinant protein, most preferably a gene represented by SEQ ID No. 6, but may include a base sequence having preferably 80% or more sequence homology, more preferably 90% or more sequence homology, and even more preferably 95% or more sequence homology to the base sequence of SEQ ID No. 6. The "% sequence homology" to a polynucleotide is confirmed by comparing a comparison region with an optimally aligned sequence, and a portion of the polynucleotide sequence in the comparison region may further include the addition or deletion (that is, a gap) compared to the reference sequence (without addition or deletion) for the optimal alignment of the sequence.

In the present specification, the "foreign peptide" is an amino acid sequence other than an amino acid sequence of an added or fused target protein during the preparation of a recombinant protein, and the type of foreign peptide is not limited as long as the foreign peptide is a peptide other than the target protein.

In the present specification, the "target protein" refers to a protein to be produced by a genetic engineering method according to the present invention, and is preferably proteins that are used for commercial use and need to be produced in large amounts, and more preferably an antigen, an antibody, a fragment of an antibody, a structural protein, a regulatory protein, a transcription factor, a toxin protein, a hormone, a hormone analog, a cytokine, an enzyme, a fragment of an enzyme, an enzyme inhibitor, a transport protein, a receptor, a fragment of a receptor, a biological defense inducer, a storage protein, a movement protein, an exploitive protein, a reporter protein, and the like, but is not limited thereto as long as the target protein is a protein that can be prepared by a recombinant vector of the present invention.

In the present specification, the "use stability" means that due to a foreign peptide added when a target protein is prepared using a recombinant vector, inherent effects in using the target protein are maximally maintained by reducing side effects, risks, differences of the effects, and the like, which are not predicted during the use of the target protein.

In the present specification, the "recombinant vector" refers to a vector capable of expressing a peptide or protein encoded by foreign nucleic acids inserted in the vector, preferably a vector prepared so as to include a new BiP gene fragment. The "vector" refers to any medium for the introduction and/or transfer of bases into a host cell in vitro, ex vivo, or in vivo, and may be a replicon to which another DNA fragment may be bound to bring about the replication of the bound fragment, and the "replicon" refers to any genetic unit (for example, a plasmid, a phage, a cosmid, a chromosome, a virus, and the like) that functions as an autonomous unit of DNA replication in vivo, that is, one which is capable of replication under its own control. The recombinant expression vector of the present invention may include preferably a promoter which is a transcription initiation factor to which an RNA polymerase is bound, any operator sequence for regulating transcription, a sequence encoding an appropriate mRNA ribosome binding site, a sequence regulating termination of transcription and decoding, a terminator, and the like, may additionally include more preferably a 5' UTR site gene of M17 for increasing the synthesis amount of a protein, an HDEL gene for minimizing the degradation of a protein such that the protein may be stably maintained in the endoplasmic reticulum, may additionally include even more preferably a tag gene for increasing the production amount of a recombinant protein, a tag gene for maintaining the structural stability of the recombinant protein, a tag gene for easily isolating the recombinant protein, a selection marker gene such as an antibiotic-resistant gene for selecting a transgenic organism, and the like, representative examples of a tag for easy isolation include an Avi tag, a Calmodulin tag, a polyglutamate tag, an E tag, a FLAG tag, a HA tag, a His tag, an Myc tag, a S tag, a SBP tag, an IgG-Fc tag, a CTB tag, a Softag 1 tag, a Softag 3 tag, a Strep tag, a TC tag, a V5 tag, a VSV tag, an Xpress tag, and the like, representative examples of the selection marker gene include an herbicide resistance gene such as glyphosate or phosphinothricin, an antibiotic resistance gene such as kanamycin, G418, bleomycin, hygromycin, and chloramphenicol, an aadA gene, and the like, representative examples of the promoter include a pEMU promoter, a MAS promoter, a histone promoter, a Clp promoter, a 35S promoter derived from the cauliflower mosaic virus, a 19S RNA promoter derived from the cauliflower mosaic virus, an actin protein promoter of a plant, a ubiquitin protein promoter, a cytomegalovirus (CMV) promoter, a simian virus 40 (SV40) promoter, a respiratory syncytial virus (RSV) promoter, an elongation factor-1 alpha (EF-1α) promoter, and the like, and representative examples of the terminator include nopaline synthase (NOS), a rice amylase RAmy1 A terminator, a phaseolin terminator, an Octopine gene terminator of *Agrobacterium tumefaciens*, an *E. coli* rrnB1/B2 terminator, and the like, but the type of added gene is not limited as long as it is a type used for the preparation of the existing recombinant protein.

In the present specification, the "transformation" collectively refers to those processes in which genetic properties of an organism are changed by injected DNA, the "transgenic organism" is an organism prepared by injecting an external gene by a molecular genetic method, preferably an organism transformed by a recombinant expression vector of the present invention, and the organism is not limited as long as it is a living organism such as a microorganism, a eukaryotic cell, an insect, an animal, and a plant, and is preferably *Escherichia coli, Salmonella, Bacillus*, yeast, an animal cell, a mouse, a rat, a dog, a monkey, a pig, a horse, a cow, *Agrobacterium tumefaciens*, a plant, and the like, but is not limited thereto. The transgenic organism may be prepared by a method such as transformation, transfection, *Agrobacterium*-mediated transformation, particle gun bombardment, sonication, electroporation, and polyethylene glycol (PEG)-mediated transformation, but is not limited as long as it is a method capable of injecting the vector of the present invention.

In the present specification, the "solubility" refers to the degree to which a target protein or peptide can be dissolved in a solvent suitable for administration to the human body. Specifically, the solubility may indicate the degree to which a solute is saturated in a given solvent at a specific temperature. The solubility may be measured by determining the saturation concentration of the solute, and for example, an excessive amount of solute is added to a solvent, the resulting mixture is stirred and filtered, and then the concentration may be measured using a UV spectrophotometer, HPLC, or the like, but the method for measuring solubility is not limited, and high solubility is advantageous for the isolation and purification of a recombinant protein, and has an advantage in that aggregation of the recombinant protein is inhibited, and thus physiological activity or pharmacological activity of the recombinant protein is maintained.

Hereinafter, preferred examples for helping the understanding of the present invention will be suggested. However, the following Examples are provided only to more easily understand the present invention, and the contents of the present invention are not limited by the following Examples.

EXAMPLES

Example 1: Confirmation of Residue of BiP Peptide During the Preparation of Recombinant Protein During the preparation of a recombinant protein, when a BiP peptide sequence used in order to move the recombinant protein to the endoplasmic reticulum is moved to the endoplasmic reticulum, the BiP peptide sequence is expected to be removed by a signal peptidase, but no study on this has been conducted. The present inventors performed experiments in order to confirm whether a residue of the BiP peptide was present in the prepared recombinant protein.

1.1. Preparation of Swine Fever Antigen E2 Protein Fused with Cellulose-Binding Domain In order to confirm the residue of the BiP peptide, first, a recombinant vector for preparing a swine fever antigen E2 protein fused with a cellulose-binding domain (CBD) was primarily prepared. More specifically, a recombinant vector was constructed by cloning a 5' untranslated region site gene (SEQ ID No. 1) of M17, a polynucleotide (SEQ ID No. 2) encoding a chaperone binding protein (BiP) protein, a polynucleotide (SEQ ID No. 3) encoding a swine fever antigen E2 protein, a polynucleotide (SEQ ID No. 4) encoding a cellulose-binding domain, and a polynucleotide encoding a His-Asp-Glu-Leu (HDEL) protein in this order between a CaMV 35S promoter gene of a pCAMBIA1300 vector and a NOS terminator. And then, a transformed plant body was prepared by transforming *Arabidopsis thaliana* with the recombinant vector by *Agrobacterium*-mediated transformation, selecting *A. thaliana* having resistance to kanamycin, and finally securing a homo seed in which the expression of an E2 recombinant protein fused with a cellulose-binding domain is stabilized. And then, a recombinant protein was isolated from 5 g of the transformed plant body using a protein extraction buffer universally used to extract a protein and amorphous cellulose (AMC). And then, the isolated recombinant protein was dialyzed using phosphate-buffered saline (PBS), and then concentrated using a centrifugal filter tube.

1.2. Confirmation of Residue of BiP Peptide

In order to confirm a residue of the BiP peptide, the N-terminal sequence of the recombinant protein was analyzed using a protein sequencing system (Prociose491/PPSQ) of the Korea Basic Science Institute (KBSI). For the new sequencing, the E2 protein fused with the cellulose-binding domain prepared as in Example 1.1 was added to phosphate-buffered saline (PBS) supplemented with 1% cellobiose so as to have a concentration of 0.4 mg/mL, and amino acid sequencing was performed according to the protocol of the sequencing system.

As a result, it was confirmed that other than the sequence of the E2 protein, an additional sequence of BiP of "IEE-ATKL" and an "RIQ" linker sequence added during the cloning procedure were present.

Example 2: Preparation of NS1 Recombinant Protein Using New BiP Sequence

In order to enhance the use stability of the recombinant protein by minimizing a foreign peptide other than a target protein which is one of the important elements in the production of the recombinant protein, an experiment was performed to prepare a new BiP sequence (SEQ ID No. 7) from which 7 amino acids were removed, which were fused at the N-terminal site of the target protein among the BiP residue confirmed through Example 1, such that a new BiP (NB) gene fragment was prepared by removing a portion of the remaining BiP residue in the recombinant protein.

2.1. Preparation of Recombinant Vector Including New BiP Sequence and Preparation of Recombinant Protein Using Said Vector In order to prepare a recombinant vector including the new BiP gene fragment represented by SEQ ID No. 6, the recombinant vector was constructed by cloning a 5' untranslated region (UTR) site gene (SEQ ID No. 1) of M17, a new BiP gene fragment (SEQ ID No. 6), and a polynucleotide (SEQ ID No. 8) encoding an NS1 protein of Zika virus (Zika NS1) in this order between a CaMV 35S promoter gene of a pCAMBIA1300 vector and a NOS terminator. And then, after an NS1 recombinant protein was expressed by a transient expression method of inoculating *Agrobacterium tumefaciens* transformed with the vector onto leaves of a tobacco plant (*Nicotiana benthamiana*), a protein was extracted from the plant leaves and centrifuged. And then, a histidine-tag conjugated recombinant protein was isolated by using a Ni-NTA column to perform immobilized metal affinity chromatography (IMAC). And then, the isolated recombinant protein was dialyzed using phosphate-buffered saline (PBS), and then concentrated using a centrifugal filter tube.

2.2. Confirmation of Residue of New BiP Peptide

In order to confirm the residue of the new BiP peptide, the N-terminal sequence of the recombinant protein was analyzed in the same manner as in Example 1.2. The results are illustrated in FIG. 1.

As illustrated in FIG. 1, it was confirmed that there was no BiP residue sequence except for the NS1 protein sequence, and an amino acid "GS" linker sequence added during the cloning procedure was present. Through the result, it was confirmed that alone with the new BiP peptide sequence moved normally to the endoplasmic reticulum, and the recombinant protein was also prepared normally.

Example 3: Preparation of RVGe Recombinant Protein Using New BiP Sequence

3.1. Preparation of Recombinant Vector Including New BiP Sequence and Preparation of Recombinant Protein Using Said Vector In order to prepare a recombinant vector including the new BiP gene fragment represented by SEQ ID No. 7 and a glycoprotein which is a main antigen of Rabies virus, the recombinant vector was constructed by cloning a 5' untranslated region (UTR) site gene (SEQ ID No. 1) of M17, a new BiP gene fragment (SEQ ID No. 6), and a polynucleotide (SEQ ID No. 9) encoding a Rabies virus glycoprotein (RVGe) in this order between a CaMV 35S promoter gene of a pCAMBIA1300 vector and a NOS terminator. As a control, a recombinant vector was constructed by inserting the existing BiP gene instead of the new BiP gene. And then, after an NS1 recombinant protein was expressed by a transient expression method of inoculating *Agrobacterium tumefaciens* transformed with the vector onto leaves of a tobacco plant (*Nicotiana benthamiana*), a protein was extracted from the plant leaves and centrifuged. During the protein extraction, a 20 mM sodium phosphate (pH 7.3) solution supplemented with 0.1% Triton X-100, 20 mM imidazole (pH 7.5), and 300 mM NaCl was used.

3.2. Experiment Confirming Expression Level of Recombinant Protein

Western blotting was performed on the entire protein extract including the recombinant protein expressed in the same manner as in Example 3.1 using an anti-His antibody. The results are illustrated in FIG. 2.

Figure 2:
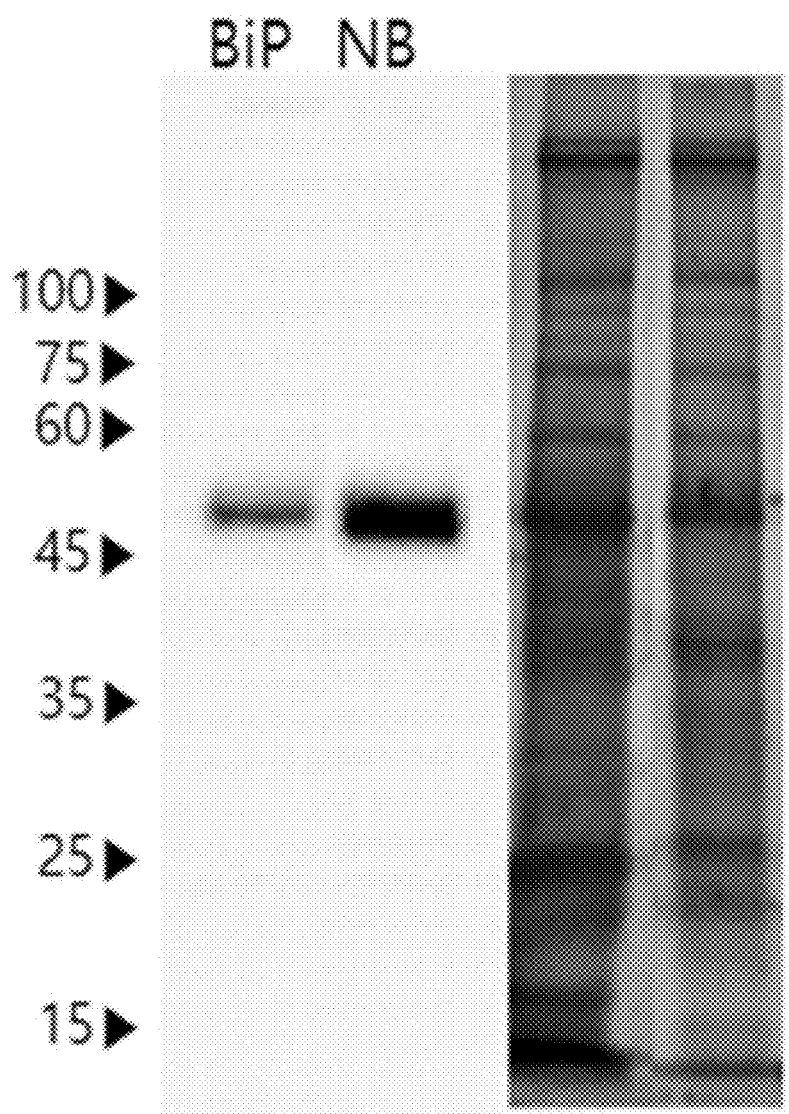
FIG. 2 is a view illustrating results confirming the production amount and solubility of an RVGe protein to which a new BiP fragment according to an example of the present invention is bound via western blotting.

As illustrated in FIG. 2, it was confirmed that when the polynucleotide encoding the new BiP peptide sequence (BiP) was used, the amount of protein was increased by about two times or more as compared to the case where the polynucleotide encoding the existing BiP peptide sequence was used. Through the result, it was confirmed that when the recombinant protein was prepared using the new BiP peptide sequence, the production amount of recombinant protein could be increased.

Through the results, it could be confirmed that when the new BiP sequence of the present invention was used for the preparation of a recombinant protein, the recombinant protein could be prepared and the production amount of recombinant protein could be remarkably increased, using various target proteins. Further, it could be confirmed that the use stability of the recombinant protein could be enhanced by minimizing the addition of a foreign sequence other than the target protein. Accordingly, it could be confirmed that the use of the new BiP sequence of the present invention was greatly helpful for the efficient production of various recombinant proteins.

The above-described description of the present invention is provided for illustrative purposes, and the person skilled in the art to which the present invention pertains will understand that the present invention can be easily modified into other specific forms without changing the technical spirit or essential features of the present invention. Therefore, it should be understood that the above-described examples are illustrative only in all aspects and are not restrictive.

INDUSTRIAL APPLICABILITY

The present invention relates to a recombinant vector comprising a new BiP gene fragment, and when a target protein is prepared using the recombinant vector of the present invention, use stability can be enhanced and the production amount of target protein can also be increased by minimizing a foreign peptide sequence remaining in the target protein, so that the recombinant vector of the present invention is expected to be able to be widely used for the production of various recombinant proteins.

The invention claimed is:

1. A gene construct in which a fragment of chaperone binding protein (BiP) gene consisting of the nucleotide sequence of SEQ ID NO. 6 and a polynucleotide encoding a target protein are sequentially linked so as to be operable, wherein the gene construct does not contain a nucleic acid sequence corresponding to positions 252-272 of SEQ ID NO:2 at a 3' terminal side immediately after the BiP gene fragment represented by SEQ ID NO. 6.

2. The gene construct of claim 1, wherein the gene construct minimizes a foreign peptide that is added in the production of the target protein, or increases the expression level of the target protein.

3. A recombinant vector comprising a gene construct in which a promoter gene, a fragment of BiP gene consisting of the nucleotide sequence of SEQ ID NO. 6, and a polynucleotide encoding a target protein are sequentially linked so as to be operable, wherein the gene construct does not contain a nucleic acid sequence corresponding to positions 252-272 of SEQ ID NO:2 at a 3' terminal side immediately after BiP gene fragment represented by SEQ ID NO. 6.

4. The recombinant vector of claim 3, wherein the gene construct minimizes a foreign peptide that is added in the production of the target protein, or increases the expression level of the target protein.

5. The recombinant vector of claim 3, wherein the promoter is any one or more selected from the group consisting of a 35S promoter derived from the cauliflower mosaic virus, a 19S RNA promoter derived from the cauliflower mosaic virus, an actin protein promoter of a plant, a ubiquitin protein promoter, a cytomegalovirus (CMV) promoter, a simian virus 40 (SV40) promoter, a respiratory syncytial virus (RSV) promoter, a pEMU promoter, an MAS promoter, a histone promoter, a Clp promoter, and an elongation factor-1 alpha (EF-1α) promoter.

6. The recombinant vector of claim 3, wherein the recombinant vector further comprises a gene encoding a His-Asp-Glu-Leu (HDEL) peptide.

7. The recombinant vector of claim 3, wherein the recombinant vector further comprises a 5' untranslated region (UTR) site gene of M17.

8. A transgenic organism transformed with the recombinant vector of claim 3.

9. A method for producing a target protein, the method comprising:

(a) culturing the transgenic organism of claim 8; and
(b) isolating and purifying a target protein from the transgenic organism or culture solution.

10. The method of claim 9, wherein the isolating of the target protein uses a sodium phosphate solution supplemented with Triton X-100, imidazole, and NaCl.

11. A transgenic organism transformed with the recombinant vector of claim 4.

12. A method for producing a target protein, the method comprising:

(a) culturing the transgenic organism of claim 11; and
(b) isolating and purifying a target protein from the transgenic organism or culture solution.

13. The method of claim 12, wherein the isolating of the target protein uses a sodium phosphate solution supplemented with Triton X-100, imidazole, and NaCl.

14. A transgenic organism transformed with the recombinant vector of claim 5.

15. A method for producing a target protein, the method comprising:

(a) culturing the transgenic organism of claim 14; and
(b) isolating and purifying a target protein from the transgenic organism or culture solution.

16. The method of claim 15, wherein the isolating of the target protein uses a sodium phosphate solution supplemented with Triton X-100, imidazole, and NaCl.

17. A transgenic organism transformed with the recombinant vector of claim 6.

18. A method for producing a target protein, the method comprising:

(a) culturing the transgenic organism of claim 17; and
(b) isolating and purifying a target protein from the transgenic organism or culture solution.

19. The method of claim 18, wherein the isolating of the target protein uses a sodium phosphate solution supplemented with Triton X-100, imidazole, and NaCl.

20. A transgenic organism transformed with the recombinant vector of claim 7.

21. A method for producing a target protein, the method comprising:

(a) culturing the transgenic organism of claim 20; and
(b) isolating and purifying a target protein from the transgenic organism or culture solution.

22. The method of claim 21, wherein the isolating of the target protein uses a sodium phosphate solution supplemented with Triton X-100, imidazole, and NaCl.

* * * * *

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: 5'UTR of M17 gene

<400> SEQUENCE: 1
ggcgtgtgtg tgtgttaaag a                                              21

<210> SEQ ID NO 2
<211> LENGTH: 272
<212> TYPE: DNA
<213> ORGANISM: Artificial Sequence
<220> FEATURE:
<223> OTHER INFORMATION: DNA sequence of chapherone binding protein(BiP)

<400> SEQUENCE: 2
atggctcgct cgtttggagc taacagtacc gttgtgttgg cgatcatctt cttcggtgag     60
tgattttccg atcttcttct ccgatttaga tctcctctac attgttgctt aatctcagaa    120 cctttttcg ttgttcctgg atctgaatgt gtttgtttgc aatttcacga tcttaaaagg    180
ttagatctcg attggtattg acgattggaa tctttacgat ttcaggatgt ttatttgcgt    240
tgtcctctgc aatagaagag gctacgaagt ta                                  272

<210> SEQ ID NO 3
<211> LENGTH: 1026
<212> TYPE: DNA
<213> ORGANISM: Artificial Sequence
<220> FEATURE:
<223> OTHER INFORMATION: DNA sequence of E2

<400> SEQUENCE: 3
aacggctagc ctgcaaggaa gattacaggt acgcaatatc atcaaccaat gagatagggc     60
tactcggggc cggaggtctc accaccacct ggaaagaata caaccacgat ttgcaactga    120
atgacgggac cgttaaggcc atttgcgtgg caggttcctt taaagtcaca gcacttaatg    180
tggtcagtag gaggtatttg gcatcattgc ataaggaggc tttacccact tccgtgacat    240
tcgagctcct gttcgacggg accaacccat caactgagga aatgggagat gacttcgggt    300
tcgggctgtg cccgtttgat acgagtcctg ttgtcaaagg aaagtacaat acaaccttgt    360
tgaacggtag tgcttctat cttgtctgtc aataggggtg gacgggtgtt atagagtgca    420
cagcagtgag cccaacaact ctgagaacag aagtggtaaa gaccttcagg agggacaagc    480
cctttccgca cagaatggat tgtgtgacca acagtggaaa aatgaagat ttattctact    540 gtaagttggg gggcaactgg acatgtgtga aggtgaacc agtggtctac acggggggc    600 tagtaaaaca atgcagatgg tgtggctttg acttcaatga gcctgacgga ctcccacact    660
accccatagg taagtgcatt ttggcaaatg agacaggtta cagaatagtg gattcaacag    720
actgtaacag agatggtgtt gtaatcagca cagagggag tcatgagtgc ttgatcggta    780
acacgactgt caaggtgcat gcatcagatg aaagactggg ccccatgcca tgcagaccta    840
aagagatcgt ctcctagtgca ggacctgtaa ggaaaacttc ctgtacattc aactacgcaa    900
aaactttgaa gaacaagtac tatgagccca gggacagcta cttccagcaa tatatgctta    960
agggcgagta tcagtactgg tttgacctgg acgtgactga ccgccactca gattacttcg   1020
cagaag                                                              1026

<210> SEQ ID NO 4
<211> LENGTH: 429
<212> TYPE: DNA
<213> ORGANISM: Artificial Sequence
<220> FEATURE:
<223> OTHER INFORMATION: DNA sequence of cellulose-binding domain

<400> SEQUENCE: 4

```
tttcgaagtt caccagtgcc tgcacctggt gataacacaa gagacgcata ttctatcatt      60
caggccgagg attatgacag cagttatggt cccaaccttc aaatctttag cttaccaggt     120
ggtggcagcg ccattggcta tattgaaaat ggttattcca ctacctataa aaatattgat     180
tttggtgacg gcgcaacgtc cgtaacagca agagtagcta cccagaatgc tactaccatt     240
caggtaagat tgggaagtcc atcgggtaca ttacttggaa caatttacgt ggggtccaca     300
ggaagctttg atacttatag ggatgtatcc gctaccatta gtaatactgc gggtgtaaaa     360
gatattgttc ttgtattctc aggtcctgtt aatgttgact ggtttgtatt ctcaaaatca     420
ggaacttct                                                             429
```

<210> SEQ ID NO 5
<211> LENGTH: 34
<212> TYPE: PRT
<213> ORGANISM: Artificial Sequence
<220> FEATURE:
<223> OTHER INFORMATION: Amino acid sequence of BiP residue

<400> SEQUENCE: 5

```
Met Ala Arg Ser Phe Gly Ala Asn Ser Thr Val Val Leu Ala Ile Ile
1               5                   10                  15

Phe Phe Gly Cys Leu Phe Ala Leu Ser Ser Ala Ile Glu Glu Ala Thr
            20                  25                  30

Lys Leu
```

<210> SEQ ID NO 6
<211> LENGTH: 251
<212> TYPE: DNA
<213> ORGANISM: Artificial Sequence
<220> FEATURE:
<223> OTHER INFORMATION: DNA sequence of new BiP

<400> SEQUENCE: 6

```
atggctcgct cgtttggagc taacagtacc gttgtgttgg cgatcatctt cttcggtgag      60
tgattttccg atcttcttct ccgatttaga tctcctctac attgttgctt aatctcagaa     120
ccttttttcg ttgttcctgg atctgaatgt gtttgtttgc aatttcacga tcttaaaagg     180
ttagatctcg attggtattg acgattggaa tctttacgat tcaggatgt ttatttgcgt      240
tgtcctctgc a                                                          251
```

<210> SEQ ID NO 7
<211> LENGTH: 27
<212> TYPE: PRT
<213> ORGANISM: Artificial Sequence
<220> FEATURE:
<223> OTHER INFORMATION: Amino acid sequence of new BiP residue

<400> SEQUENCE: 7

```
Met Ala Arg Ser Phe Gly Ala Asn Ser Thr Val Val Leu Ala Ile Ile
1               5                   10                  15

Phe Phe Gly Cys Leu Phe Ala Leu Ser Ser Ala
```

-continued 20 25

<210> SEQ ID NO 8
<211> LENGTH: 1056
<212> TYPE: DNA
<213> ORGANISM: Artificial Sequence
<220> FEATURE:
<223> OTHER INFORMATION: DNA sequence of Zika NS1

<400> SEQUENCE: 8
gatgtgggtt gctcagttga tttttctaaa aaagaaactc ggtgtgggac tggcgttttc 60
gtttacaatg atgttgaggc ttggagggat agatataaat accatccaga ttcacctaga 120
agacttgctg cagccgttaa gcaagcttgg gaggatggaa tttgtggtat aagcagtgtt 180
agtagaatgg agaatatcat gtggagatcg gtagaaggag aattgaatgc tattttggaa 240
gaaaatggtg tgcagctcac agtggttgtg ggatctgtta agaacccgat gtggcgaggt 300
ccacaacgtc ttcctgtacc tgtcaatgaa ctaccccacg gttggaaggc gtggggaaag 360
tcatatttcg ttagggcagc aaagacaaac aattcttttg ttgtagatgg cgatactctt 420
aaagagtgtc cattgaaaca tagagcttgg aactcttttt tagtcgagga tcatggattc 480
ggggtctttc acacctccgt atggctgaag gttagggagg actattcact tgaatgcgac 540
ccagcagtaa tcggcacagc tgttaaagga aaggaggctg tgcattctga cttaggttat 600
tggattgaat ctgaaaagaa tgatacttgg agactaaaga gagcccattt aatagagatg 660
aagacttgtg aatggcctaa atcacatacc ttgtggactg atgggatcga agaaagtgat 720
cttataattc ccaaatcctt ggcaggccca ctgagtcacc acaatactcg ggaagggtat 780
agaacacaaa tgaaaggtcc gtggcattct gaagaactcg aaattcgatt tgaggaatgc 840
cctggaacca aagtccatgt ggaggaaacc tgtggtacaa gaggaccttc acttagatcg 900
actacagctt caggacgtgt tattgaagaa tggtgttgca gagaatgtac gatgcctcca 960
ttgtcattcc aggctaagga tggttgctgg tacggtatgg aaattaggcc aagaaaggag 1020
cctgaaagca accttgttag gtctatggtt acagca 1056

<210> SEQ ID NO 9
<211> LENGTH: 1314
<212> TYPE: DNA
<213> ORGANISM: Artificial Sequence
<220> FEATURE:
<223> OTHER INFORMATION: DNA sequence of RVGe

<400> SEQUENCE: 9
aaattcccca tctacacgat accggataaa cttggtcctt ggtctccaat tgatattcat 60
catctcagct gtccaaataa tctggttgtc gaggatgaag ggtgtaccaa cttgtcaggt 120
ttttcctata tggaacttaa agtgggatac atttcggcca taaaagtgaa cggctttacg 180
tgcacaggtg tggtgacaga ggcggaaacg tatactaatt tcgttgggta tgtgactact 240
accttcaaaa gaaagcattt tcgcccgaca ccggacgcct gtcgggcggc ttataattgg 300
aaaatggccg gtgacccgcg ttatgaggaa tctctgcata atccgtaccc agattatcac 360
tggttacgaa ctgtgaagac cacgaaagaa agtctggtta tcatctcccc aagtgtagcg 420
gacctggacc catatgataa atctcttcac agccgcgtct ttcctaacgg aaagtgcagc 480
ggcataacga tttcttctac ctactgccct accaaccatg attacacaat ctggctgccc 540
gagaatccgc gcctgggcac atcttgcgat atttttacca acagtagagg taaacgggca 600
tctaaaggga gcaagacctg tgggtttgtt gatgaacgtg gtctgtacaa atcattgaaa 660

-continued

```
ggagcatgca aattaaaatt atgcggggtc cttgggcttc gtctgatgga tggtacgtgg    720
gtagcgatgc aggcgtcgga cgaaaccaaa tggtgccctc cagatcagct ggtaaatcta    780
cacgactttc gcagtgacga gatagaacat ctcgttgtgg aggaacttgt caaaaagcga    840
gaagaatgtt tagacgcatt agagtccatc atgactacta agtcagtgag tttccggcgt    900
ctgagccact tgcgtaaatt ggtccccggc tttggaaaag catacacaat cttcaacaag    960
acattaatgg aagctgacgc tcactataag agtgttcgca cctggaatga aataatcccc   1020
tccaaagggt gtctgcgtgt gggcgggagg tgtcatcctc atgtaaacgg cgtattttc   1080
aatggcatta tcctgggtcc tgatggccat gttctaatcc cggaaatgca atcaagcctc   1140
cttcagcaac acatggagtt gttggaatcc tcagtcatcc ccctgatgca tccgctggcc   1200
gatccgtcta cagttttcaa agatggcgat gaagcagaga actttgtgga ggttcacctt   1260
ccggatgtac ataaacagat ctcgggagtt gatctgggtc tccctaactg gggg          1314
```